US00PP19558P2

(12) United States Plant Patent
Miyazaki

(10) Patent No.: US PP19,558 P2
(45) Date of Patent: Dec. 9, 2008

(54) ***PHLOX* PLANT NAMED 'SUNPHLOTORI'**

(50) Latin Name: *Phlox drummondii*
Varietal Denomination: Sunphlotori

(75) Inventor: Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/903,797

(22) Filed: Sep. 25, 2007

(51) Int. Cl.
*A01H 5/00* (2006.01)

(52) U.S. Cl. ..... Plt./320

(58) Field of Classification Search ..... Plt./320
See application file for complete search history.

*Primary Examiner*—Kent L. Bell
*Assistant Examiner*—June Hwu
(74) *Attorney, Agent, or Firm*—C. A. Whealy

(57) ABSTRACT

A new and distinct cultivar of *Phlox* plant named 'Sunphlotori', characterized by its compact and mounding plant habit; vigorous growth habit; freely branching habit; red purple and white bi-colored flowers; freely and continuous flowering habit; and good garden performance.

1 Drawing Sheet

Botanical designation: *Phlox drummondii.*
Cultivar denomination: 'Sunphlotori'.

BACKGROUND OF THE INVENTION

The present invention relates to a new and distinct cultivar of *Phlox,* botanically known as *Phlox drummondii* and hereinafter referred to by the name 'Sunphlotori'.

The new *Phlox* is a product of a planned breeding program conducted by the Inventor in Higashiomi, Shiga, Japan. The objective of the breeding program was to create new compact *Phlox* cultivars with attractive flower coloration.

The new *Phlox* originated from a cross-pollination made by the Inventor in June, 2002, in Higashiomi, Shiga, Japan, of a proprietary selection of *Phlox drummondii* identified as code number 2Ph-52a, not patented, as the female, or seed, parent with a proprietary selection of *Phlox drummondii* identified as code number 2Ph-52b, not patented, as the male, or pollen, parent. The new *Phlox* was discovered and selected by the Inventor as a single flowering plant within the progeny of the stated cross-pollination in a controlled environment in Higashiomi, Shiga, Japan.

Asexual reproduction of the new *Phlox* by vegetative cuttings in a controlled environment in Higashiomi, Shiga, Japan since October, 2005, has shown that the unique features of this new *Phlox* are stable and reproduced true to type in successive generations.

SUMMARY OF THE INVENTION

The cultivar Sunphlotori has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunphlotori'. These characteristics in combination distinguish 'Sunphlotori' as a new and distinct cultivar of *Phlox:*

1. Compact and mounding plant habit.
2. Vigorous growth habit.
3. Freely branching habit.
4. Red purple and white bi-colored flowers.
5. Freely and continuous flowering habit.
6. Good garden performance.

Compared to plants of the parent selections, plants of the new *Phlox* are more compact and differ in flower coloration as flowers of plants of the parent selections are pale yellow color with a red purple-colored eye.

Plants of the new *Phlox* can also be compared to plants of the cultivar Grammy Pink and White, not patented. In side-by-side comparisons conducted in Higashiomi, Shiga, Japan, plants of the new *Phlox* and the cultivar Grammy Pink and White differed in the following characteristics:

1. Plants of the new *Phlox* were broader, more vigorous and more freely branching than plants of the cultivar Grammy Pink and White.
2. Plants of the new *Phlox* had smaller leaves than plants of the cultivar Grammy Pink and White.
3. Plants of the new *Phlox* had smaller inflorescences than plants of the cultivar Grammy Pink and White.

BRIEF DESCRIPTION OF THE PHOTOGRAPHS

The accompanying colored photographs illustrate the overall appearance of the new *Phlox,* showing the colors as true as it is reasonably possible to obtain in colored reproductions of this type. Colors in the photographs may differ slightly from the color values cited in the detailed botanical description which accurately describe the colors of the new *Phlox.*

The photograph at the top of the sheet comprises a top perspective view of a typical flowering plant of 'Sunphlotori' grown in a container.

The photograph at the bottom of the sheet is a close-up view of typical flowers of 'Sunphlotori'.

DETAILED BOTANICAL DESCRIPTION

The aforementioned photographs and following observations, measurements and values describe plants grown in Higashiomi, Shiga, Japan, under commercial practice during the summer in an outdoor nursery with day temperatures ranged from 15° C. to 33° C. and night temperatures ranging from 13° C. to 25° C. After planting, plants were pinched one time. Plants had been growing for about five months when the photographs and description were taken. In the following description, color references are made to The Royal Horticultural Society Colour Chart, 2001 Edition, except where general terms of ordinary dictionary significance are used.

Botanical Classification: *Phlox drummondii* cultivar Sunphlotori.

Parentage:

*Female, or seed, parent.*—Proprietary selection of *Phlox drummondii* identified as code number 2Ph-52a, not patented.

*Male, or pollen, parent.*—Proprietary selection of *Phlox drummondii* identified as code number 2Ph-52b, not patented.

Propagation:

*Type.*—By vegetative cuttings.

*Time to initiate roots.*—About two to three weeks at 20° C. to 25° C.

*Time to produce a rooted young plant roots.*—About one to two months at 20° C. to 25° C.

*Root description.*—Fine, fibrous and fleshy; ivory white to pale brown in color.

*Rooting habit.*—Freely branching.

Plant description:

*Plant form/habit.*—Compact and mounded plant habit; outwardly spreading; vigorous growth habit. Freely branching habit; pinching enhances branching potential.

*Plant height.*—About 12.8 cm.

*Plant width* (*spread*).—About 22.2 cm.

*Lateral branches.*—Length: About 5.8 cm. Diameter: About 1 mm. Internode length: About 6 mm. Strength: Strong. Texture: Pubescent. Color: 144A.

Foliage description:

*Arrangement.*—Alternate, simple; sessile.

*Length.*—About 1.7 cm.

*Width.*—About 6 mm.

*Shape.*—Lanceolate.

*Apex.*—Acute.

*Base.*—Obtuse.

*Margin.*—Entire.

*Texture, upper and lower surfaces.*—Pubescent.

*Venation pattern.*—Pinnate; reticulate.

*Color.*—Developing and fully expanded leaves, upper surface: 137A; venation, 144A. Developing and fully expanded leaves, lower surface: 137C; venation, 144A.

Flower Description:

*Flower type/habit.*—Single rotate hypocraterimorphous flowers arranged in terminal and axillary cymes; flowers face obliquely upward to outward. Freely flowering habit with about two to three flowers per cyme.

*Fragrance.*—None detected.

*Natural flowering season.*—Continuously flowering from spring to autumn in Higashiomi, Shiga, Japan. Flowers not persistent.

*Postproduction longevity.*—Flowers last about five days on the plant.

*Flower buds.*—Height: About 1.4 cm. Diameter: About 3 mm. Shape: Clavate. Color: 77B.

*Inflorescence height.*—About 2.4 cm.

*Inflorescence diameter.*—About 4.6 cm.

*Flower diameter.*—About 2.2 cm.

*Flower depth.*—About 2 cm.

*Throat diameter.*—About 1.5 mm.

*Tube length.*—About 1.2 cm.

*Petals.*—Quantity per flower: Typically five in a single whorl; petals fused at the base into a narrow tube. Length: About 1.1 cm. Lobe width: About 1 cm. Shape: Cordate. Apex: Emarginate. Margin: Entire; weakly undulate. Texture, upper and lower surfaces: Sparsely pubescent. Color: Developing petals, upper surface: Close to 155C; towards the margin, apex, base and random spots and streaks, N74A; central longitudinal stripe, 143B; throat, close to 72A. Developing petals, lower surface: Close to N78C; central longitudinal stripe, 143B; tube, 76B. Fully expanded petals, upper surface: Close to 155C; towards the margin, apex, base and random spots and streaks, N74A; central longitudinal stripe, 143D; throat, close to 72A. Fully expanded petals, lower surface: Close to N78C; central longitudinal stripe, 143B; tube, 76B.

*Sepals.*—Quantity per flower: Typically five in a single whorl, fused at base; tubular in shape. Length: About 3 mm. Width: About 1.1 mm. Shape: Lanceolate. Apex: Acute. Margin: Entire. Texture, upper and lower surfaces: Smooth, glabrous. Color, upper and lower surfaces: 137A.

*Peduncles.*—Length: About 7 mm to 10 mm. Diameter: About 2.7 mm. Texture: Smooth, glabrous. Color: 144A.

Pedicels. —Length: About 2.3 mm. Diameter: About 0.7 mm. Texture: Pubescent. Color: 144A.

*Reproductive organs.*—Stamens: Quantity per flower: Typically five. Stamen length: About 7 mm to 12 mm. Anther shape: Lanceolate. Anther length: About 2.5 mm. Anther color: 15B. Pollen amount: Scarce. Pollen color: 17C. Pistils: Quantity per flower: One. Pistil length: About 5 mm. Stigma shape: Transversely ellipsoidal. Stigma color: 145D. Style color: 145D. Ovary color: 144B.

*Seed/fruit.*—Seed and fruit development have not been observed.

Disease/pest resistance:

Plants of the new *Phlox* have not been noted to be resistant to pathogens and pests common to *Phlox*.

Garden performance:

Plants of the new *Phlox* have been observed to have good garden performance and tolerate rain, wind and temperatures from about 0° C. to about 35° C.

It is claimed:

1. A new and distinct *Phlox* plant named 'Sunphlotori' as illustrated and described.

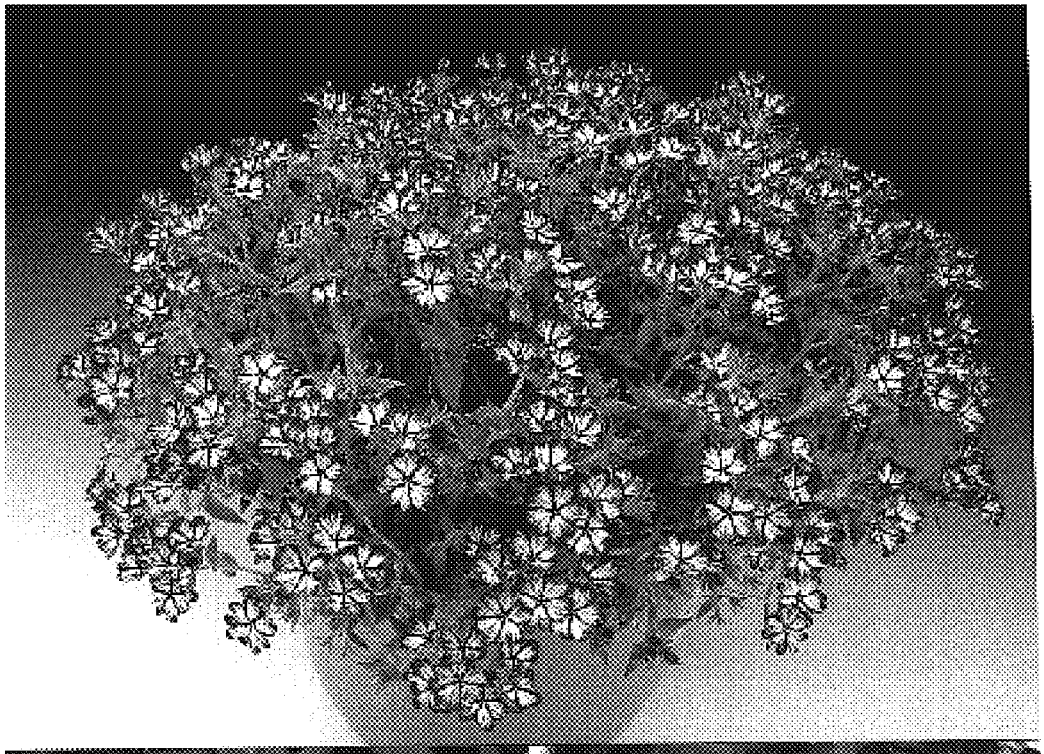
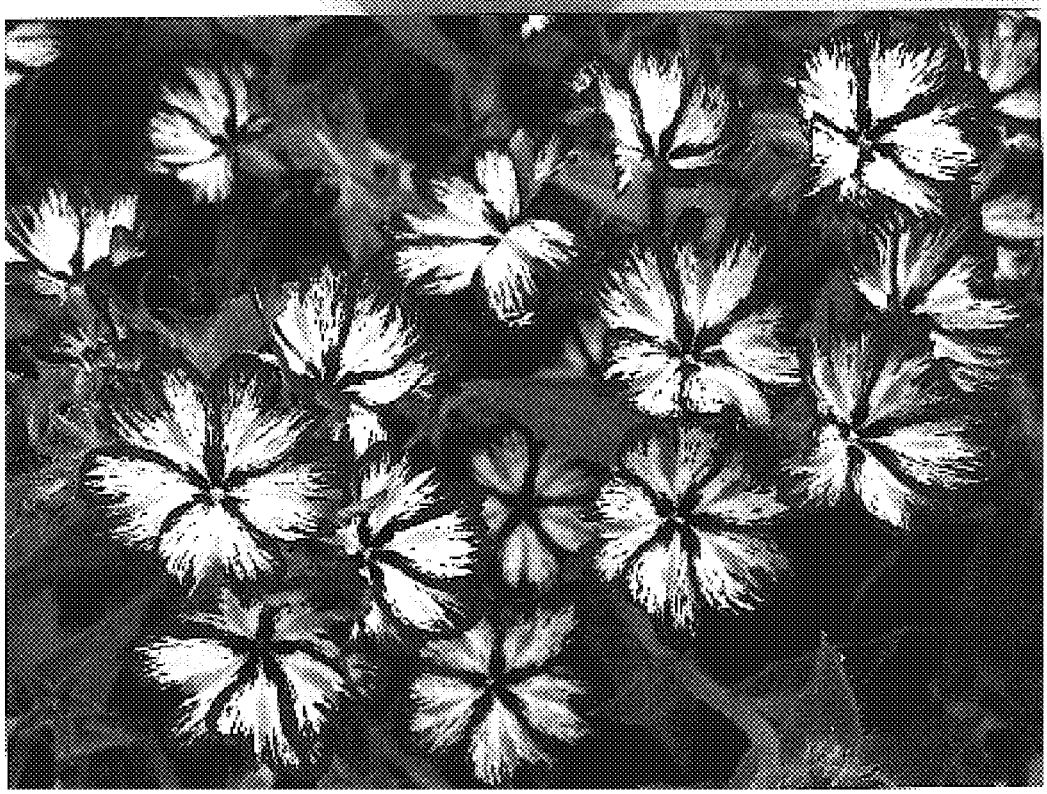

* * * * *